(12) United States Patent
Ullrich et al.

(10) Patent No.: US 7,632,645 B1
(45) Date of Patent: Dec. 15, 2009

(54) EGF RECEPTOR TRANSACTIVATION BY G-PROTEIN-COUPLED RECEPTORS REQUIRES METALLOPROTEINASE CLEAVAGE OF PROHB-EGF

(75) Inventors: Axel Ullrich, München (DE); Norbert Prezel, München (DE); Esther Zwick-Wallasch, München (DE); Henrik Daub, Regensburg (DE)

(73) Assignee: Max-Planck-Gesellschaft zur forderung der Wissenschaften e.V., Munich (DE)

( * ) Notice: Subject to any disclaimer, the term of this patent is extended or adjusted under 35 U.S.C. 154(b) by 0 days.

(21) Appl. No.: 09/461,090

(22) Filed: Dec. 14, 1999

(30) Foreign Application Priority Data

Aug. 16, 1999 (EP) ................. 99116056

(51) Int. Cl.
*G01N 33/53* (2006.01)
*G01N 33/566* (2006.01)
*C07K 16/00* (2006.01)
*C12K 21/08* (2006.01)

(52) U.S. Cl. .............. 435/7.1; 436/501; 530/388.22
(58) Field of Classification Search .............. 435/6, 435/7.1, 91.1, 91.2, 183, 23; 436/94, 501; 536/23.1, 24.3, 24.33, 25.3; 530/300, 350, 530/388.22
See application file for complete search history.

(56) References Cited

FOREIGN PATENT DOCUMENTS

| EP | 0 780 386 | 6/1997 |
|---|---|---|
| EP | 0 780 386 A1 | 6/1997 |

OTHER PUBLICATIONS

Dong et al., Metalloproteinase -mediated ligand release regulates autocrine signaling through the epidermal growth factor receptor. Proc. Natl. Acad. Sci. USA 96, 6235-6240, May 1999.*
Daub et al., Signal characteristics of G protein-transactivated EGF receptor. EMBO J. 16, 7032-7044, Dec. 1997.*
Khandaker et al., Metalloproteinases are involved in lipopolysacharide- and tumor necrosis factor-alpha-mediated regulation of CXCR1 and CXCR2 chemokine receptor expression. Blood 93, 2173-2185, Apr. 1999.*
Dong et al., Metalloproteinase -mediated ligand release regulates autocrine signaling through the epidermal growth factor receptor. Proc. Natl. Acad. Sci. USA 96, 6235-6240, 1999.*
Daub et al., Signal characteristics of G protein-transactivated EGF receptor. EMBO J. 16, 7032-7044, 1997.*
Dong et al., Metalloproteinase -mediated ligand release regulates autocrine signaling through the epidermal growth factor receptor. Proc. Natl. Acad. Sci. USA 96, 6235-6240, 1999.*
Daub at al., Signal characteristics of G protein-transactivated EGF receptor. EMBO J. 16, 7032-7044, 1997.*
Gura, Science, 278, 1041 and 1042, Nov. 1997.*
Rosendahl, Mary, et al., Identification and Characterization of a Pro-tumor necrosis factor . . . , The Journal of Biological Chemistry, 1997, vol. 272, pp. 24588-24593.*
Kaushal, Gur., The new kids on the block: ADAMTSs, potentially multifunctional metalloproteinases of the ADAM family, The Journal of Clinical Investigation, May 2000, vol. 105, pp. 1335-1337.*
Miyoshi, Eiji, Membrane-anchored Heparin-binding Epidermal Growth Factor-like Growth Factor Acts as a Tumor Survival . . . , May 1997, vol. 272, pp. 14349-14355.*
Tiruppathi et al., G protein-coupled receptor kinase-5 regulates thrombin-activated signaling in endothelial cells. PNAS, 97, 7440-7445, Jun. 2000.*
Sherwood et al., Epidermal growth factor receptor activation in androgen-independent but not androgen-stimulated growth of human prostatic carcinoma cells. British Journal of Cancer, 77, 855-861, Mar. 1998.*
Klemke et al., Receptor tyrosine kinase signaling required for integrin alpha v beta 5-directed cell motility but not adhesion on vitronectin. The Journal of Cell Biology, 127, 859-866, 1994.*
White et al., What in vitro models of infection can and cannot do. Pharmacotherapy, 21, 292S-301S, 2001.*
The definition for receptor tyrosine kinases from Wikipedia, the free encyclopedia. Printed on Sep. 23, 2008. The definition for ErbB from Wikipedia, the free encyclopedia. Printed on Sep. 24, 2008.*
Wezker et al., Transactivation joins multiple tracks to the ERK/MAPK cascade. Nature Reviews Molecular Cell Biology, 4, 651-657, 2003.*
Nishida et al., Localization of CD9, an Enhancer Protein for Proheparin-Binding Epidermal Growth Factor-Like Growth Factor, in Human Atherosclerotic Plaques: Possible Involvement of Juxtacrine Growth Mechanism on Smooth Muscle Cell Proliferation. Arterioscler. Thromb. Vasc Biol., 20, 1236-1243, 2000.*

(Continued)

*Primary Examiner*—Frank W Lu
(74) *Attorney, Agent, or Firm*—Rothwell, Figg, Ernst & Manbeck, P.C.

(57) ABSTRACT

The present invention relates to agents and methods for growth-factor receptor activation by modulating the G-protein mediated signal transduction pathway.

1 Claim, 19 Drawing Sheets

OTHER PUBLICATIONS

Dong et al., "Metalloprotease-mediated ligand release regulates autocrine signaling through the epidermal growth factor receptor", Proceedings of the National Academy of Science s of the United States of America, May 25, 1999, vol. 96, No. 11.

Brown et al., "cell surface ectodomain cleavage of human amphiregulin precursor is sensitive to a metalloprotease inhibitor", Journal of Biological Chemistry, vol. 273, No. 27, 1998, pp. 17258-17268.

Daub et al., "role of transactivation of the EGF receptor in signaling by G-protein-coupled receptors", Nature, vol. 379, 1996, pp. 557-560.

Daub et al., "signal characteristics of g protein transactivated EGF receptor", EMBO Journal, vol. 16, No. 23, 1997, pp. 7032-7044.

lzumi et al., "a metalloprotease disintegrin, mdc9/meltrin-gamma/adam9 and pkcdelta re involved in tpa induced ectodomain shedding of membrane anchored heparin binding egf like growth factor", EMBO Journal, vol. 17, No. 24, 1998, pp. 7260-7272.

Werb, "ecm and cell surface proteolysis: regulating cellular ecology", Cell, vol. 91, 1997, pp. 439-442.

Takeyama et al., "Epidermal growth factor system regulates mucin production in airways", "Proceedings of the National Academy of Sciences of the United States of America", Mar. 16, 1999, vol. 96, No. 6, Mar. 16, 1999, vol. 96, No. 6.

Romano et al., "*Helicobacter pylori* upregulates expression of epidermal growth factor related peptides, but inhibits their proliferative effect in mkn 28 gastric mucosa cells", Journal of Clinical Investigation, vol. 101, No. 8, 1998, pp. 1604-1613.

James K. Liao, "Shedding growth factors in cardiac hypertrophy", Nature Medicine, vol. 8, No. 1, Jan. 2002.

Asakura et al., "Cardiac hypertrophy is inhibited by antagonism of ADAM12 processing of HB-EGF: Metalloproteinase inhibitors as a new therapy", Nature Medicine, vol. 8, No. 1, Jan. 2002.

Dong et al., "Metalloprotease-mediated ligand release regulates autocrine signaling through the epidermal growth factor receptor", Proc. Natl. Acad. Sci., vol. 96, pp. 6235-6240, May 1999, Cell Biology.

Brown et al., "Cell Surface Ectodomain Cleavage of Human Amphiregulin Precursor is Sensitive to a Metalloprotease Inhibitor", The Journal of Biological Chemistry, vol. 273, No. 27, Issue of Jul. 3, pp. 17258-17268, 1998.

Daub et al., "Role of transactivation of the EGF receptor in signalling by G-protein-coupled receptors", Letters to Nature, vol. 379, Feb. 8, 1996, pp. 557-560.

Daub et al., "Signal characteristics of G protein-transactivated EGF receptor", The EMBO Journal, vol. 16, No. 23, pp. 7032-7044, 1997.

lzumi et al., "A Metalloprotease-disintegrin, MDC9/meltrin-γ/ADAM9 and PKCδ are involved in TPA-induced ectodomain shedding of membrane-anchored heparin-binding EGF-like growth factor", The EMBO Journal, vol. 17, No. 24, pp. 7260-7272, 1998.

Zena Werb, "ECM and Cell Surface Proteolysis: Regulating Cellular Ecology", Cell, vol. 91, pp. 439-442, Nov. 14, 1997.

Takeyama et al., "Epidermal growth factor system regulates mucin production in airways", Proc. Natl. Acad. Sci., vol. 96, pp. 3081-3086, Mar. 1999, Medical Sciences.

Romano et al., "*Helicobacter pylori* Upregulates Expression of Epidermal Growth Factor-related Peptides, but Inhibits Their Proliferative Effect in MKN 28 Gastric Mucosal Cells", The Journal of Clinical Investigation, vol. 101, No. 8, Apr. 1998, pp. 1604-1613.

Prenzel et al., "EGF receptor transactivation by G-protein-coupled receptors requires metalloproteinase cleavage of proHB-EGF", Nature, vol. 402, Dec. 23-30, 1999, pp. 884-888.

* cited by examiner

EGF RECEPTOR TRANSACTIVATION BY G-PROTEIN-COUPLED RECEPTORS REQUIRES METALLOPROTEINASE CLEAVAGE OF PROHB-EGF

The present invention relates to agents and methods for modulating growth-factor receptor activation by modulating G-protein mediated signal transduction.

Crosstalk between different signalling systems allows the integration of a great diversity of stimuli that a cell receives under varying physiological situations. Transactivation of EGF receptor-dependent signalling pathways upon stimulation of G-protein-coupled receptors (GPCR) which are critical for the mitogenic activity of ligands such as LPA, endothelin, thrombin, bombesin and carbachol represents evidence for such an interconnected communication network. The mechanism of this cross-communication is not understood, but based on reported data it was proposed to be transmitted by intracellular elements[1-4].

We report here that activation of growth-factor receptors such as epidermal growth-factor receptor (EGFR) upon GPCR stimulation requires the receptor's extracellular domain. As key element of this mechanism we identify a membrane-spanning growth-factor ligand precursor, such as proHB-EGF, and a proteinase activity that is rapidly induced upon GPCR-ligand interaction. We show that inhibition of growth-factor precursor processing blocks GPCR-induced growth-factor receptor transactivation and downstream signals. As evidence for the pathophysiological significance of this mechanism we demonstrate inhibition of constitutive EGFR activity upon treatment of human PC-3 prostate carcinoma cells with the metalloproteinase inhibitor batimastat. Together, these results establish a new mechanistic concept for crosstalk among different signalling systems.

Further, the results demonstrate the importance of proteinases as targets for the treatment or prevention of diseases which are associated with pathological growth-factor receptor overexpression.

In a first aspect the invention relates to the use of modulators of G-protein mediated signal transduction for the manufacture of an agent which modulates growth-factor receptor activation. Preferably the activation of the growth-factor receptor is mediated by its extracellular domain and via an extracellular signal pathway. Thus the modulator may act on cells which are heterologous to the growth-factor receptor carrying target cells. The growth-factor receptor activation preferably occurs by tyrosine phosphorylation, by which an intracellular signal cascade is mediated. Examples of suitable growth-factor receptors are EGFR, and other members of the EGFR family such as HER-2, HER-3 or HER-4, but also other growth-factor receptors such as TNF receptor 1, TNF receptor 2, CD 30 and IL-6 receptor.

The modulator of the G-protein mediated signal transduction may act on one or several compounds of the signal transduction pathway. Particularly, the modulator may act on a G-protein, a G-protein coupled receptor, a proteinase and/or a growth-factor precursor which are key elements of the signal transduction pathway. Preferably the modulator acts on a proteinase.

The substrate which is subject to cleavage by the protease is preferably a growth-factor receptor ligand precursor. This precursor is preferably a membrane-associated molecule. In a particularly preferred example the growth-factor ligand precursor is proHB-EGF which is cleaved to HB-EGF and the growth-factor receptor is EGFR. Other preferred examples of growth-factor ligands which are cleaved from precursors are other members of the EGF family such as TGFα, amphiregulin, epiregulin, EGF, betacellulin, members of the heregulin/NDF family including isoforms thereof and TNFα.

The proteinase which is modulated is usually a membrane-associated proteinase, preferably a metalloproteinase such a zinc-dependent proteinase. Examples of these proteinases are members of the ADAM family. The modulation of proteinase activity may comprise a stimulation or inhibition. Preferably the proteinase activity is inhibited which in turn results in an inhibition of growth-factor receptor activation.

The modulation of proteinase activity is preferably effected by adding an acitvator or inhibitor of proteinase activity to the system which in a particulary preferred embodiment directly modulates the proteinase activity. A preferred example for such a modulator for proteinase activity is the proteinase inhibitor batimastat. Further examples are marimastat (British Biotech), TAPI (Immunex) and TIMP-1, -2, -3 or -4, particularly TIMP-3[31]. Still a further example is CRM197, a catalytically inactive form of the diphtheria toxin, which specifically binds to proHB-EGF and which is capable of blocking the processing of proHB-EGF by metalloproteinases.

The modulation of G-protein modulated signal transduction has great significance for diagnostic and clinical applications. For example, the modulation of G-protein mediated signal transduction is a target for the prevention or treatment of disorders associated with or accompanied by a disturbed e.g. pathologically enhanced growth-factor receptor activation. More particularly, the present invention provides methods for preventing or treating, among other diseases, hyperproliferative diseases such as colon, pancreatic, prostate, gastric, breast, lung, thyroid, pituitary, adrenal and ovarian tumors, as well as thyroid hyperplasia, retinitis pigmentosa, precocious puberty, acromegaly and asthma. More particulary, the growth of human prostate cancer cells may be inhibited by treatment with proteinase inhibitors such as batimastat.

Thus, the present invention provides a method for modulating growth-factor activation comprising contacting a cell or an organism which contains a growth-factor receptor capable of being activated with a modulator of G-protein mediated signal transduction. The contacting step may occur in vitro, e.g. in a cell culture or in vivo, e.g. in a subject in the need of medical treatment, preferably a human. The active agent is added in an amount sufficient to modulate growth-factor receptor activation, particularly in an amount sufficient to inhibit growth-factor receptor activation at least partially. Preferably the active agent is administered as a pharmaceutically acceptable composition, which may contain suitable diluents, carriers and auxiliary agents. The composition may also contain further pharmaceutically active agents e.g. cytotoxic agents for the treatment of cancer.

Pharmaceutical compositions suitable for use in the present invention include compositions wherein the active ingredients are contained in an effective amount to achieve its intended purpose. A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g. for determining the LD50 (the dose lethal to 50% of the population) and the ED50 (the dose therapeutically effective in 50% of the population). For any compound used in the method of the invention, the therapeutically effective dose can be estimated initially from cell culture assays. For example, a dose can be formulated in animal models to achieve a circulating concentration range that includes the IC50 as determined in cell culture (i.e. the concentration of the test compound which achieves a half-maximal inhibition of the growth-factor receptor activity). Such information can be used to more accurately determine useful doses in humans. The dose ratio between toxic and therapeutic effects is the therapeutic index and it can be expressed as the ratio between LD50 and ED50. Compounds which exhibit high therapeutic indices are preferred. The exact formulation, route of administration and dosage can be chosen by the individual physician in view of the patient's condition (see e.g. Fingl et al., 1975, in "The Pharmacological Basis of Therapeutics", Ch. 1, p. 1).

Dosage amount and interval may be adjusted individually to provide plasma levels of the active moiety which are sufficient to maintain the receptor modulating effects, or minimal effective concentration (MEC), The MEC will vary for each compound but can be estimated from in vitro data, e.g. the concentration necessary to achieve a 50-90% inhibition of the receptor using the assays described herein. Compounds should be administered using a regimen which maintains plasma levels above the MEC for 10-90% of the time, preferably between 30-90% and most preferably between 50-90%. Dosages necessary to achieve the MEC will depend on individual characteristics and route of administration. In cases of local administration or selective uptake, the effective local concentration of the drug may not be related to plasma concentration.

The actual amount of composition administered will, of course, be dependent on the subject being treated, on the subject's weight, the severity of the affliction, the manner of administration and the judgement of the prescribing physician. For batimastat, and other compounds e.g. a daily dosage of 1 to 200 mg/kg, particularly 10 to 100 mg/kg per day is suitable.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systematic manner, for example, via injection of the compound directly into a solid tumor, often in a depot or sustained release formulation.

Furthermore, one may administer the drug in a targeted drug delivery system, for example in a liposome coated with a tumor-specific antibody. The liposomes will be targeted to and taken up selectively by the tumor.

Still a further aspect of the present invention is a method for identifying and providing modulators of G-protein mediated signal transduction comprising contacting a cell which contains a growth-factor receptor capable of being activated with a test compound suspected to be a modulator of G-protein mediated signal transduction and determining the degree of growth-factor receptor activation. This method is suitable as a high-throughput screening procedure for identifying novel compounds or classes of compounds which are capable of modulating G-protein signal transduction. Further, the present invention encompasses any novel modulator identified by the disclosed method.

In a preferred embodiment of the invention cell lines expressing G-protein coupled receptors and/or metalloproteinases may be used to screen for and identify compounds that inhibit the activity of growth-factor receptors.

The ability of test compounds to inhibit the activity of growth-factor receptors extracellulary activated by G-protein coupled receptor mediated signalling pathways can be determined as described in the examples.

Further, the present invention is described in detail by the following figures and examples:

g) Unstarved PC-3 cells were treated for indicated times with DMSO or batimastat and EGFR tyrosine phosphorylation was monitored with αPY immunoblot.

EXAMPLES

1. Methods

Cloning and plasmids

The following plasmids have been described: pcDNA1-BombR and pcDNA3-M1R[1]. For stable expression of the M1R in Rat-1 cells the receptor was subcloned into pLXSN. pro-HB-EGF and the Endothelin receptor were amplified by PCR from a MCF-7 or Rat-1 cDNA library and subcloned into pcDNA3-VSV or pcDNA3, respectively.

Cells and transfections

Rat-1 cells and COS-7 cells were grown and infected or transfected, respectively, as described[1,2]. Rat-1HERc cells have been described elsewhere[1]. HEK 293 cells were grown in DMEM containing 10% fetal calf serum (FCS) and transfections were carried out using the Ca-phosphate method. CRM 197 (10 µg/ml,Sigma) or batimastat (BB-94), (5 µM, British Biotech) were added 20 minutes before the respective growth-factor. Tyrphostin AG1478 (250 nM, Calbiochem) and AG1295 (1 µM, Calbiochem) were added 15 minutes before stimulation.

Immunoprecipitation and Western blotting

The antibodies against human EGFR (108.1), SHP-2, Shc and Gab1 have been characterized[1,12,19,2]. Western blotting against the EP-R chimera was performed using rabbit polyclonal α-hPDGFRβ antibody (Upstate Biotechnology). Cells were lysed and proteins were subsequently immunoprecipitated as described[1]. To precipitate the VSV-tagged HB-EGF a monoclonal VSV antibody (P5D4, Boehringer) in combination with Protein G-Sepharose was used, HB-EGF was detected with antibody C-18 (Santa-Cruz). Due to the small size of pro-HB-EGF and the processed form of HS-EGF we used the Tricine SDS-PAGE system established by Schlägger as described[30].

Flow cytometry analysis

COS-7 cells were seeded in 6 cm-dishes; 20h later cells were washed and cultured for a further 24 h in serum-free medium until treatment with growth factors as indicated. After collection cells were incubated with goat αHB-EGF antibody (R&D Systems) for 30 minutes on ice. After washing with PBS, cells were incubated with FITC-conjugated rabbit anti-goat antibody (Sigma) for 20 minutes on ice. Cells were analysed with FACSCalibur (Becton Dickinson).

2. Results

Epidermal growth-factor receptor (EGFR) transactivation was identified as a critical element in mitogenic signalling[1,5,6] induced by G-protein-coupled receptors (GPCR), regulation of chloride channels[7], as well as modulation of potassium channel activity[8]. Since the process was found to be very rapid[1,7,9], and GPCR-induced release of EGFR ligands into the cell culture medium could not be detected[6,8], EGFR transactivation has been generally assumed to be exclusively mediated via intracellular signals[3,4].

Figure 1A:
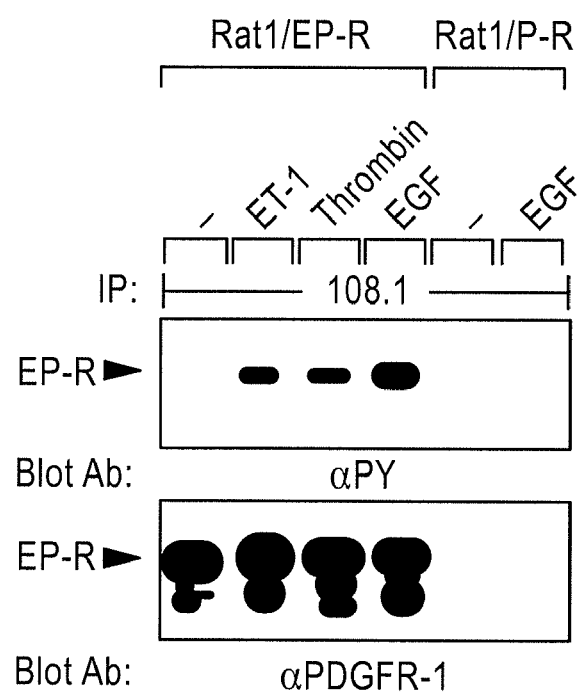
FIG. 1 GPCR-induced EP-R transactivation redefines endogenous EGFR-mediated signalling to PDGFR-specific signals. Proteins were immunoblotted with αPY antibody (4G10).
  a) Rat-1/EP-R cells were 3 minutes treated with ET-1 (200 nM), thrombin (2 U/ml) and EGF (2 ng/ml) or
  b) preincubated with tyrphostins as indicated prior to thrombin stimulation and EP-R was selectively precipitated with mAb 108.1.
  c) Different stable Rat-1 cell lines were untreated or
  d) 1 h preincubated with EGFR-E Ab ICR-3R (20 μg/ml), stimulated for 3 minutes with GPCR agonists, EGF or PDGF-BB (25 ng/ml) as indicated and SHP-2 was precipitated.
  e) Rat-1/EP-R were treated as in b) and SHC was immunoprecipitated.
Figure 1B:
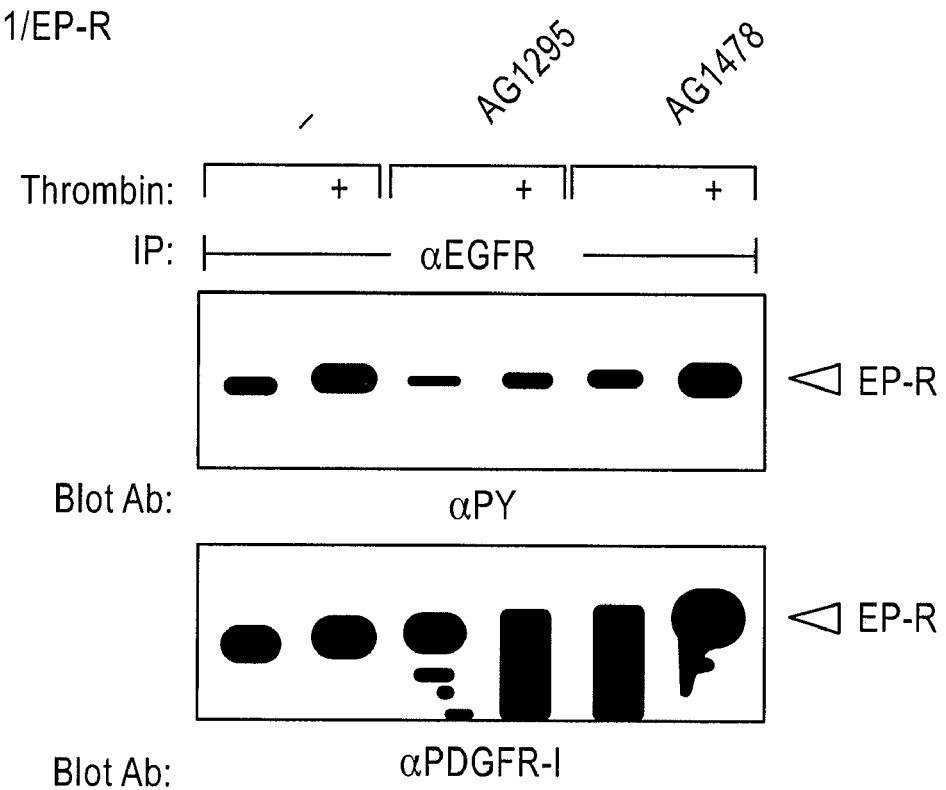
Figure 1C:
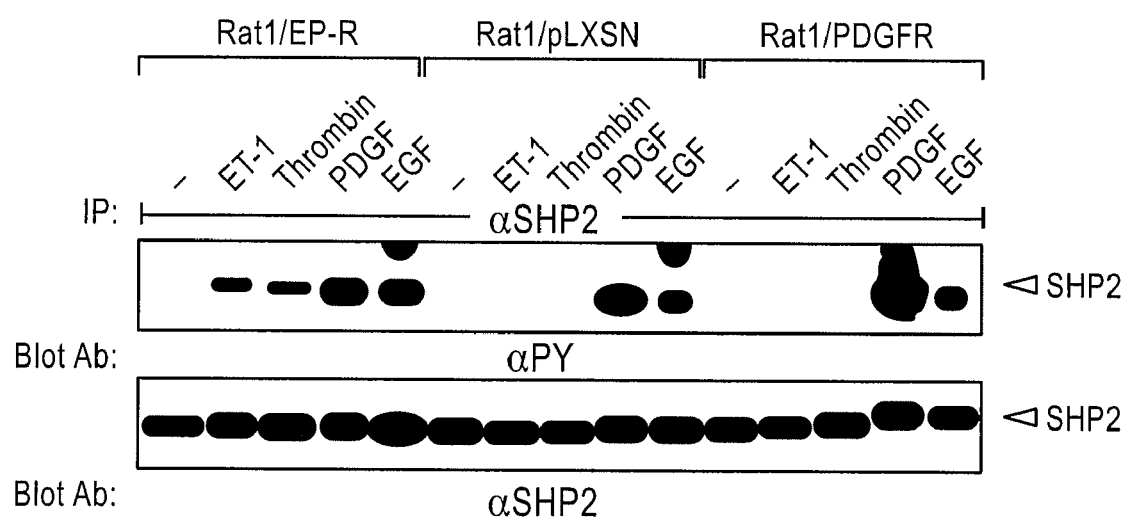
Figure 1D:
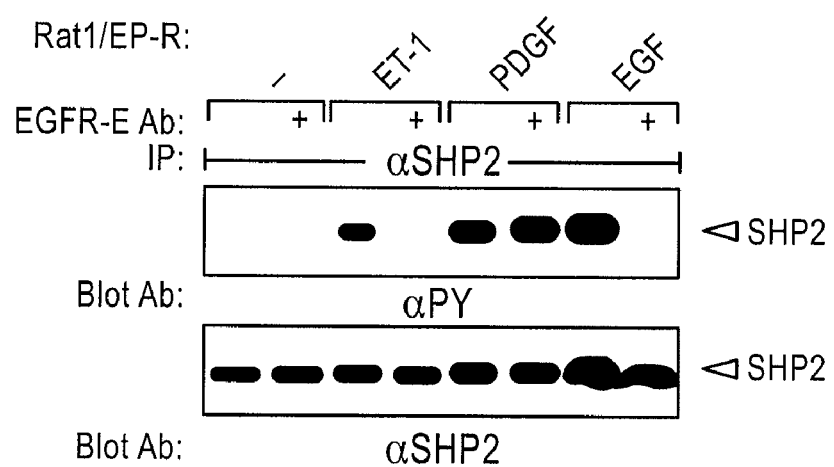
Figure 1E:
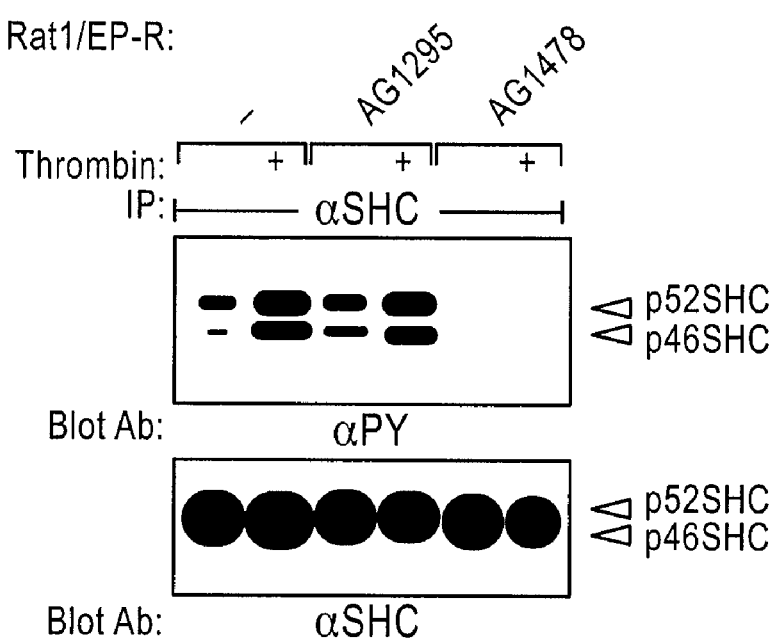

Surprisingly, however, even though PDGF receptors are not transactivated upon treatment of Rat-1 cells with GPCR ligands[2], this was the case for a chimera EP-R consisting of an EGFR extracellular and the platelet-derived growth-factor receptor (PDGFR) transmembrane and cytoplasmic signalling domain[10] (FIG. 1a). This receptor chimera immunoprecipitates with monoclonal antibody 108.1 which recognizes the extracellular portion of human but not rat EGFR. Treatment of Rat-1/EP-R cells with the PDGFR inhibitor AG1295[11], but not with the EGFR kinase antagonist AG1478[1], blocked thrombin-induced tyrosine phosphorylation of the chimeric receptor (FIG. 1b), which clearly demonstrated a critical function of the EGFR extracellular domain for GPCR-mediated transactivation. As shown in FIG. 1c, this EP-R transactivation results in a PDGF-characteristic downstream signal, since the SH2 domain-containing phosphatase 2 (SHP-2), a preferred mediator of PDGFR signalling[12], was tyrosine phosphorylated upon endothelin (ET-1) and thrombin stimulation of Rat-1 /EP-R cells, while exposure to the same ligands did not induce SHP-2 tyrosine phosphoryation in Rat-1 cells overexpressing the PDGFR or control cells. Pretreatment of Rat-1 /EP-R cells with monoclonal antibody ICR-3R[13] that blocks ligand binding to the human EGFR resulted in complete inhibition of ET-1 and EGF-induced SHP-2 tyrosine phosphorylation, whereas the PDGF-mediated response was not affected (FIG. 1d), confirming that GPCR-induced transactivation of the EP-R chimera depends on the extracellular EGFR domain. In contrast to the results obtained for SHP-2 (FIG. 1c), tyrosine phosphorylation of the adaptor protein SHC following thrombin stimulation was completely blocked by pretreatment of Rat-1/EP-R cells with AG1478, but remained unaffected by preincubation with the PDGFR antagonist AG1295 (FIG. 1e). This confirms that thrombin transactivates endogenuos rat EGFR in Rat-1/EP-R cells resulting in SHC tyrosine phosphorylation, whereas activation of the EP-R chimera redefines thrombin stimulation to generate a PDGFR-characteristic SHP-2 signal.

Figure 2A:
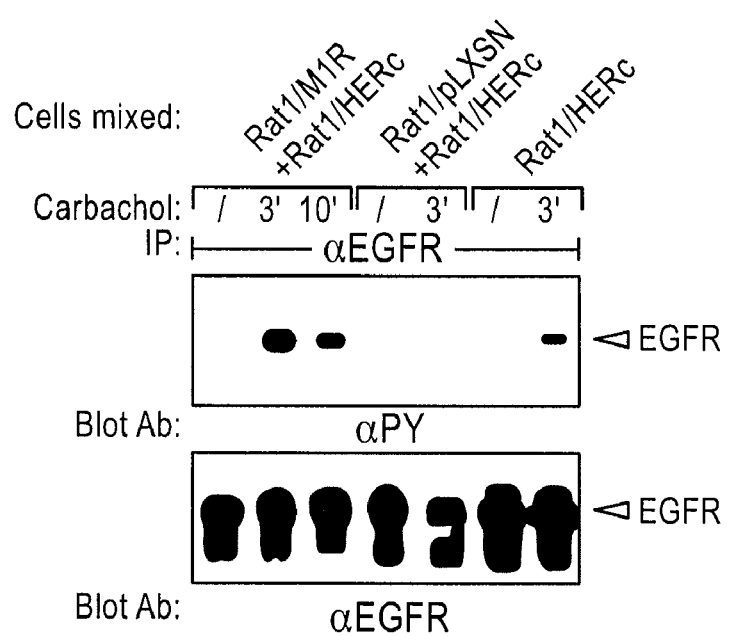
FIG. 2 Carbachol-induced intercellular transactivation of the EGF receptor. Stable Rat-1 cell lines either expressing M1R or HERc and control cells were mixed in 1:3 ratio. In
  a) after stimulation with carbachol (1 mM), HERc was precipitated and immunoblotted with αPY antibody.
  b) Co-cultures of Rat-1/M1R and Rat-1/HERc cells were planted in different densities, preincubated with EGFR-E blocking Ab ICR-3R (20 μg/ml) and HERc was precipitated following carbachol-stimulation.
  c) High density co-cultures of Rat-1 /M1R and Rat-1/HERc cells were incubated with heparitinase or chlorate and HERc was precipitated following carbacol- or EGF-stimulation.
Figure 2B:
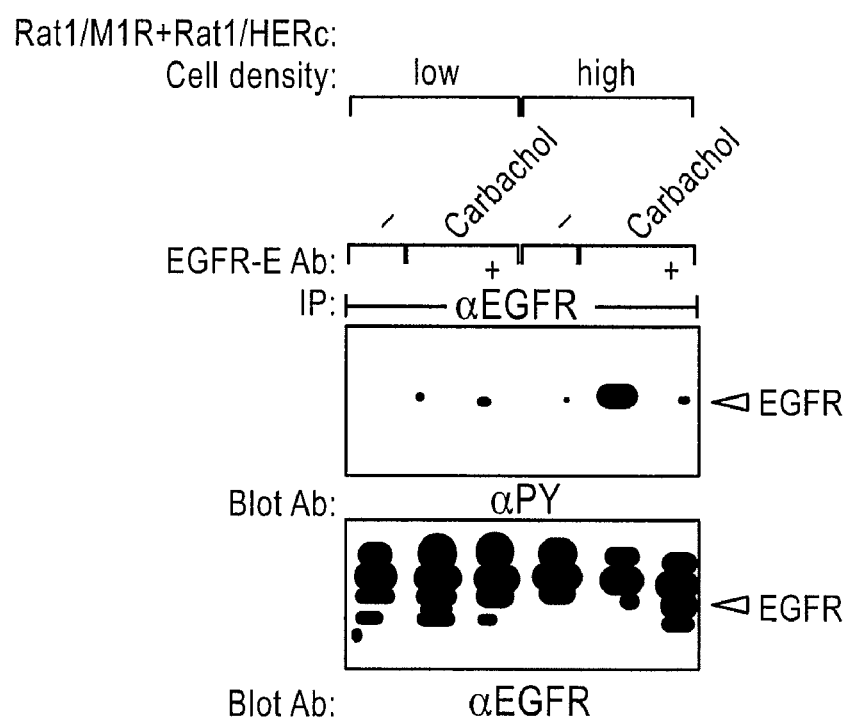
Figure 2C:
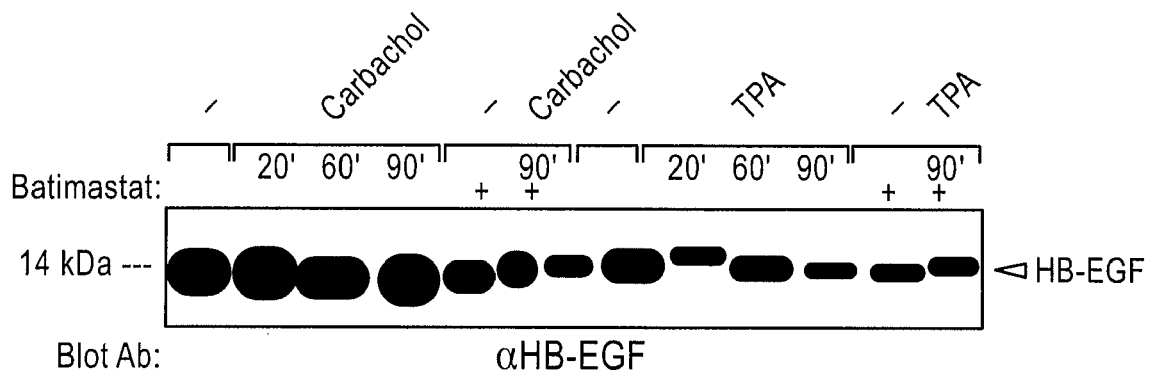
Figure 2C:
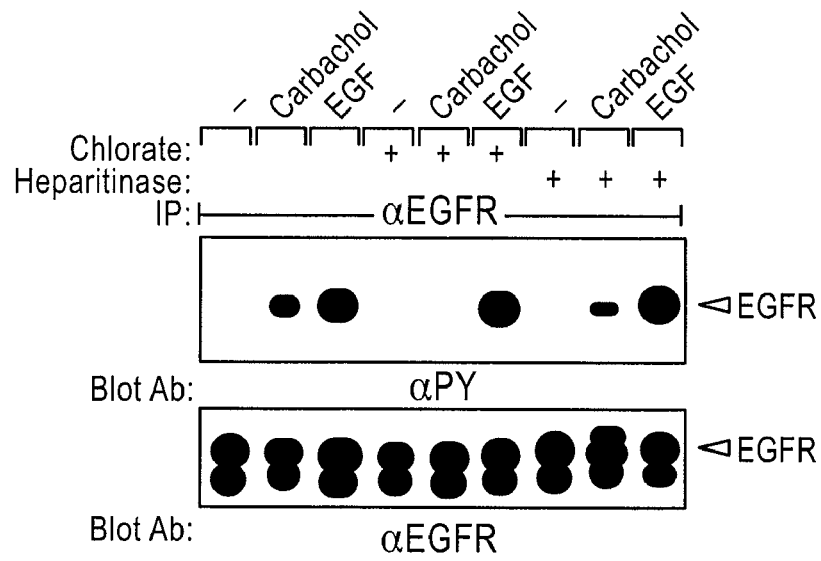

To address the question whether the extracellular signal which activates the EP-R chimera acts via an autocrine or paracrine mode, we performed a co-culture experiment with Rat-1 cells either stably overexpressing the M1 muscarinic acetylcholine receptor (M1R) or the human EGFR (HERc) at a ratio of one to one. Stimulation of the Rat-1/M1R+Rat-1/HERc co-culture with the M1R agonist carbachol prior to immunoprecipitation with human EGFR-specific antibody 108.1, rapidly induced tyrosine phosphorylation of HERc (FIG. 2a). Since neither of the control cells responded to carbachol, this result clearly demonstrated the possibility of transactivation between two cells. To investigate the influence of cell density on this paracrine process, HERc was immunoprecipitated from subconfluent versus confluent co-cultures of Rat-1/M1R and Rat-1/HERc cells following stimulation with carbachol. As shown in FIG. 2b and 2c, EGFR tyrosine phosphorylation in response to M1R agonist only occurred in confluent co-cultures and was completely inhibited by preincubation with ICR-3R antibody, heparitinase or chlorate. This further demonstrated the requirement of the EGFR ligand binding function for intercellular signal transmission and the necessity of close cell-cell contact. Together, these results lead us to conclude that EGF-like ligands, synthesized as transmembrane precursors and converted to the mature form by proteolytic cleavage[14], may be involved in GPCR-mediated transactivation. The discrepancy between previous results obtained from medium-transfer experiments[6,8] in which EGF-like ligands could not be detected upon GPCR activation and our finding of density-dependent intercellular crosstalk might be due to a scenario in which upon proteolytic processing EGF-like ligands remain with the heparin sulfate proteoglycan matrix prior to interaction with their high-affinity receptors as shown for fibroblast growth-factors[15].

Figure 3A:
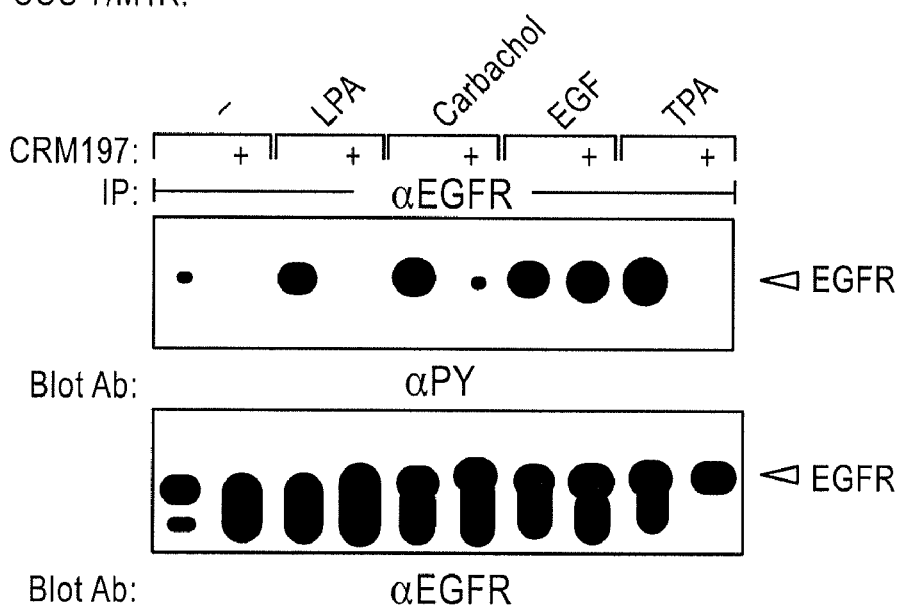
FIG. 3 GPCR-induced EGFR transactivation and adapter protein tyrosine phosphorylation is dependent on HB-EGF function. a), c), d) COS-7 and b) HEK 293 cells, transfected with the M1R or ET-R, respectively, untreated or CRM197 preincubated, were stimulated for 3 minutes with the GPCR agonists LPA (10 μM) or Carbachol (1 mM), EGF (2 ng/ml) or 1 μM TPA (5 min) as indicated. Subsequently EGFR (a,b), SHC (c) or Gab 1(d) was immunoprecipitated and proteins were immunoblotted with αPY antibody (4G10).
Figure 3B:
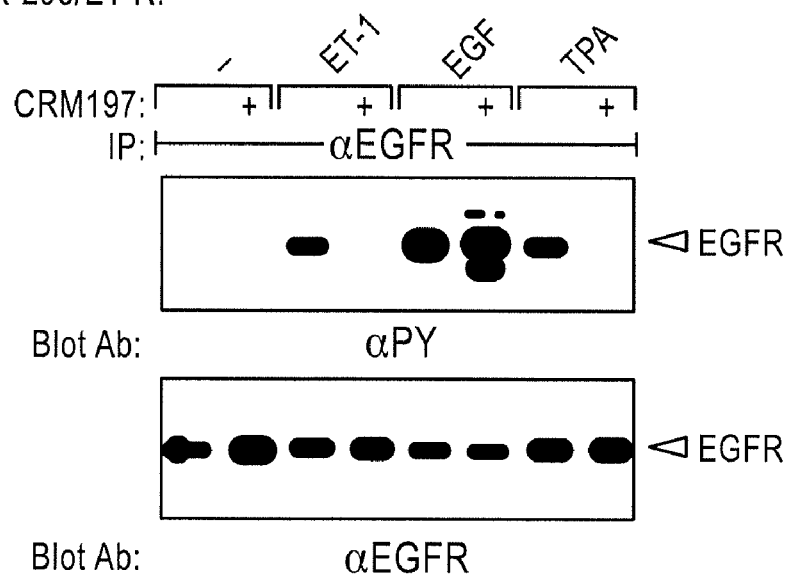

Ectodomain shedding has been shown to be induced by stimuli such as activators of heterotrimeric G-proteins, $AIF_4$ and $GTP\gamma S$[16], as well as the PKC activator tetradecanoyl-phorbol-13-acetate (TPA) and the $Ca^{2+}$-ionophore ionomycin[17,18]. The latter, which induces HB-EGF release in prostate epithelial cells[18], has recently been shown to be a potent activator of EGFR transactivation in PC12 cells[19], and TPA has been reported to induce EGFR tyrosine phosphorylation in HEK 293 cells[8]. HB-EGF, a member of the EGF family, has the ability to bind to cell surface heparan sulfate proteoglycans[20], which prevents the immediate release of the growth-factor and increases the local growth factor concentration in the cellular microenvironment. Based on these properties the proHB-EGF precursor matched our proposed requirement for GPCR-induced EGFR transactivation. Besides its function as a growth-factor precursor, proHB-EGF serves as a high-affinity receptor for diphteria toxin (DT)[21], CRM197, a non toxic mutant of DT, was shown to inhibit strongly and specifically the mitogenic activity of HB-EGF[22]. Therefore, we tested the influence of CRM197 on GPCR-mediated EGFR transactivation. We found that CRM 197 pretreatment completely inhibits tyrosine phosphorylation of the EGFR induced by the GPCR agonists lysophosphatidic acid (LPA) or carbachol as well as TPA in COS-7 cells (FIG. 3a). Inhibition was also observed for ET-1 or TPA-stimulated HEK 293 cells transiently transfected with the endothelin receptor (FIG. 3b). In contrast, EGF-induced receptor tyrosine phosphorylation was unaltered demonstrating CRM197 specificity. Furthermore, complete abrogation of LPA- and carbachol-induced receptor tyrosine phosphorylation suggested that HB-EGF is the only growth-factor mediating EGFR transactivation in the cell lines presented here.

Figure 3C:
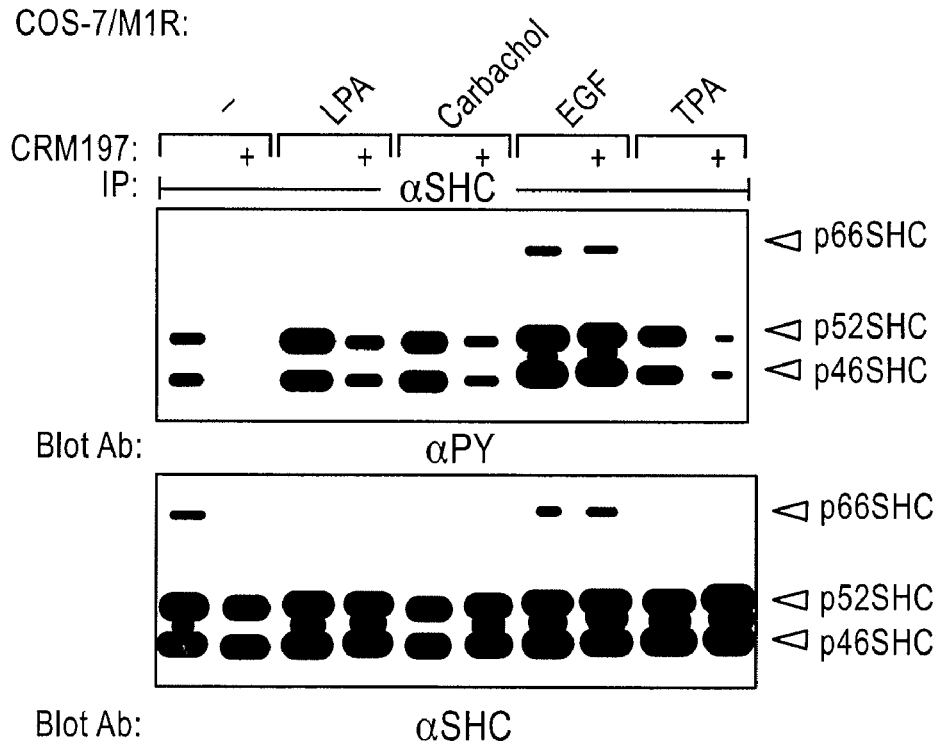
Figure 3D:
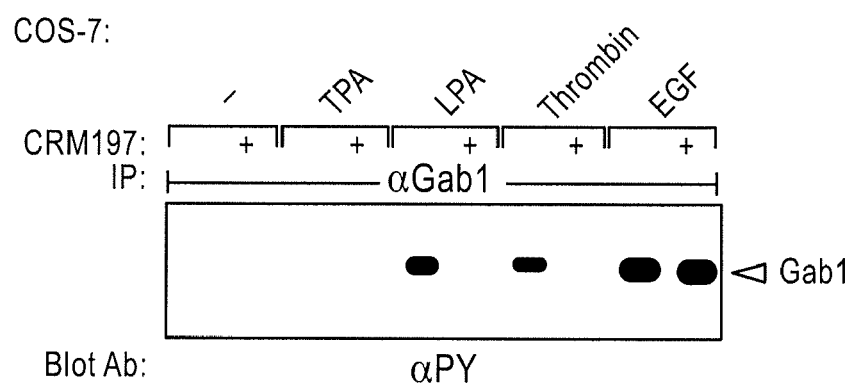

Tyrosine phosphorylation of the adaptor protein SHC is considered to be a critical step in the coupling of GPCR activation to Ras-dependent signalling pathways[23]. In order to investigate the role of HB-EGF in this process, we examined the effect of the diphteria toxin mutant CRM197 on GPCR ligand and TPA-mediated SHC tyrosine phosphorylation. As shown in FIG. 3c, in COS-7 cells, LPA-, carbachol- and TPA-induced SHC tyrosine phosphorylation was dramatically reduced by CRM197 pretreatment, while the EGF-mediated response was not affected. The same inhibitory effect of CRM197 was observed in HEK 293 cells (data not shown). Similarly, in COS-7 cells, tyrosine phosphorylation of the multidocking protein Gab1 in response to LPA or thrombin was not detected in the presence of CRM197 (FIG. 3d) confirming its signalling position downstream of the EGFR[2].

Figure 4A:
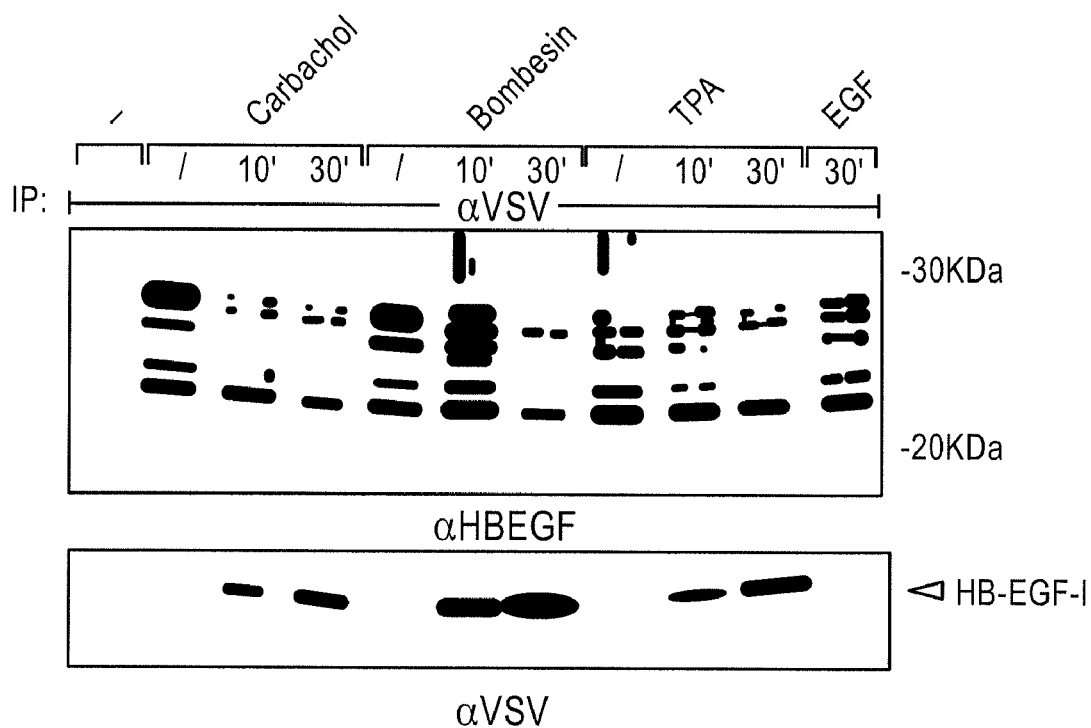
FIG. 4 GPCR-induced proteolytic processing of proHB-EGF and EGFR transactivation are critically dependent on metalloproteinase function.
  a) COS-7 cells were co-transfected with either M1R or BombR (0.5 μg each) and VSV-proHB-EGF (0.7 μg) and stimulated with carbachol (1 mM), bombesin (200 nM), TPA (1 μM) or EGF (2 ng/ml). ProHB-EGF was analysed with αHB-EGF Ab (upper part), cleaved VSV-HB-EGF was monitored by anti VSV immunoblotting (lower part).
  b) COS-7 cells transfected as in a) were preincubated with batimastat (5 μM, 30 min), stimulated as indicated and anti-VSV immunoprecipitates were subjected to αHB-EGF immunoblotting.
  c) Flow cytometric analyses of proHB-EGF in COS-7 cells treated for 10 minutes with LPA, TPA, EGF or batimastat preincubation following LPA stimulation.
  d,e) COS-7 cells, transfected with the M1R, untreated or BB-94 preincubated, were stimulated as in FIG. 3a) and EGFR (d) or SHC (e) were immunoprecipitated. Proteins were immunoblotted with αPY antibody (4G10).
  f) PC-3 cells were serum-starved for 36 hours, preincubated with batimastat and stimulated for 3 minutes with bombesin, TPA or EGF (7 ng/ml) as indicated. EGFR was immunoprecipitated and immunoblotted with αPY antibody.

Next, in order to examine whether proHB-EGF is proteilytically processed upon stimulation of GPCRs, we transfected plasmids containing VSV-tagged proHB-EGF in COS-7 cells together with the M1R or the bombesin receptor (BombR) and stimulated with respective ligands for different times. TPA, a potent inducer of proHB-EGF processing, or EGF were added as positive and negative controls, respectively. FIG. 4a shows that as previously described proHB-EGF is expressed in form of heterogenous translation products of 20 to 30 KDa[17], which can be detected with antibodies against the C-terminus of the precursor (upper panel) or the VSV-tag (lower panel). Stimulation with carbachol or bombesin led to a rapid breakdown of the membrane-anchored growth-factor precursor and proteolytic cleavage was concommitant with the appearance of the 9 KDa VSV-tagged HB-EGF fragment containing the transmembrane anchor. Interestingly, under these conditions the GPCR signal induced proteolytic proHB-EGF processing as fast and potently as TPA. As for TPA[17], GPCR-induced conversion of proHB-EGF is an extremely rapid process that generates mature HB-EGF. In contrast to GPCR-induced tyrosine phosphorylation of endogenous EGFR which is fast and transient[1,7,9], overexpression of the protease substrate VSV-proHB-EGF led to a rapid but more sustained ectodomain cleavage of proHB-EGF.

Figure 4B:
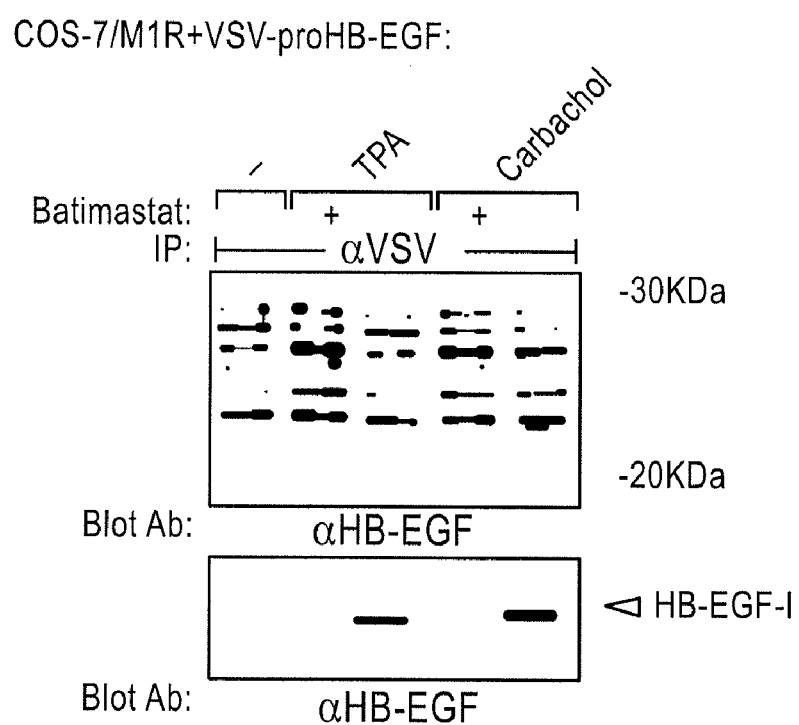

Since zinc-dependent metalloproteinases have been implicated in pro-HB-EGF shedding by TPA[24], we analysed carbachol-induced processing in the presence of batimastat (BB-94)[25], a protease inhibitor which has recently been shown to block proteolytic maturation of human amphiregulin[26]. As shown in FIG. 4b, BB-94 treatment significantly reduced HB-EGF processing in response to carbachol supporting our conclusion that metalloproteinases are critical elements in GPCR-induced HB-EGF generation and EGFR activation. In contrast thereto, PGL-hydroxamate, an MMP-specific inhibitor has no effect on LPA- or carbachol-induced transactivation (not shown).

Figure 4C:
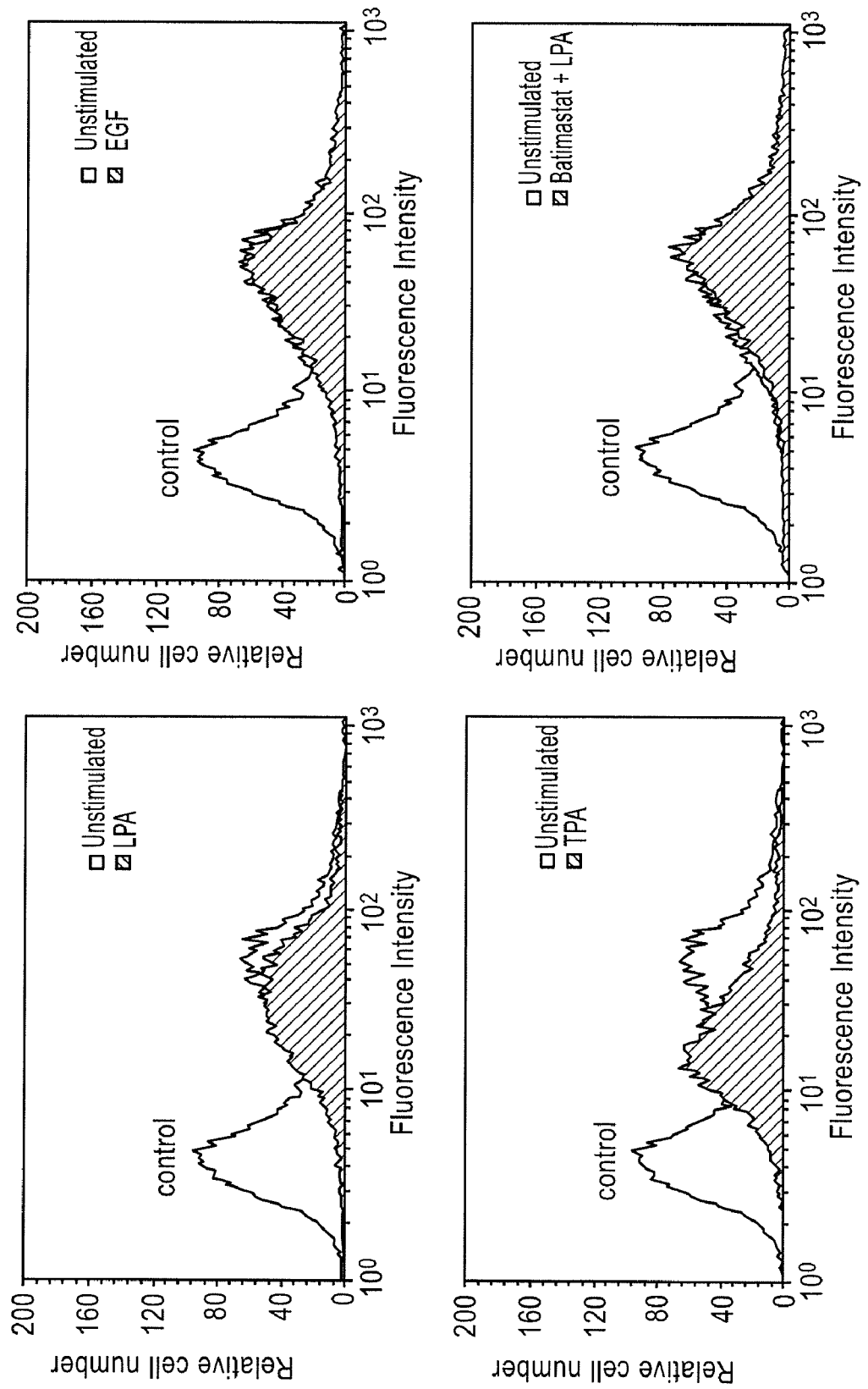

To confirm GPCR-induced proHB-EGF processing, we used an ectodomain-specific antibody and flow cytometry upon treatment of non-transfected COS-7 cells with LPA, TPA or EGF. Within 10 minutes after addition of LPA and TPA, the content of cell surface proHB-EGF was reduced while EGF stimulation showed no effect (FIG. 4c). In contrast to the experiments with transfected cells shown in FIGS. 4a and b, activation of endogenous LPA receptors was not as potent as TPA to induce proteolytic cleavage of proHB-EGF. Nonetheless, consistent with FIG. 4b, the modest LPA-induced effect was completely inhibited by batimastat.

Figure 4D:
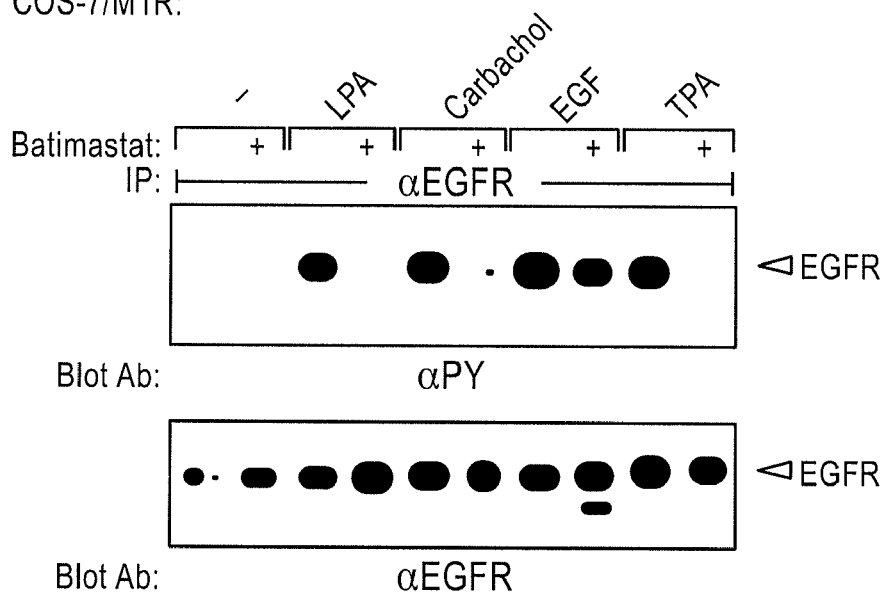
Figure 4E:
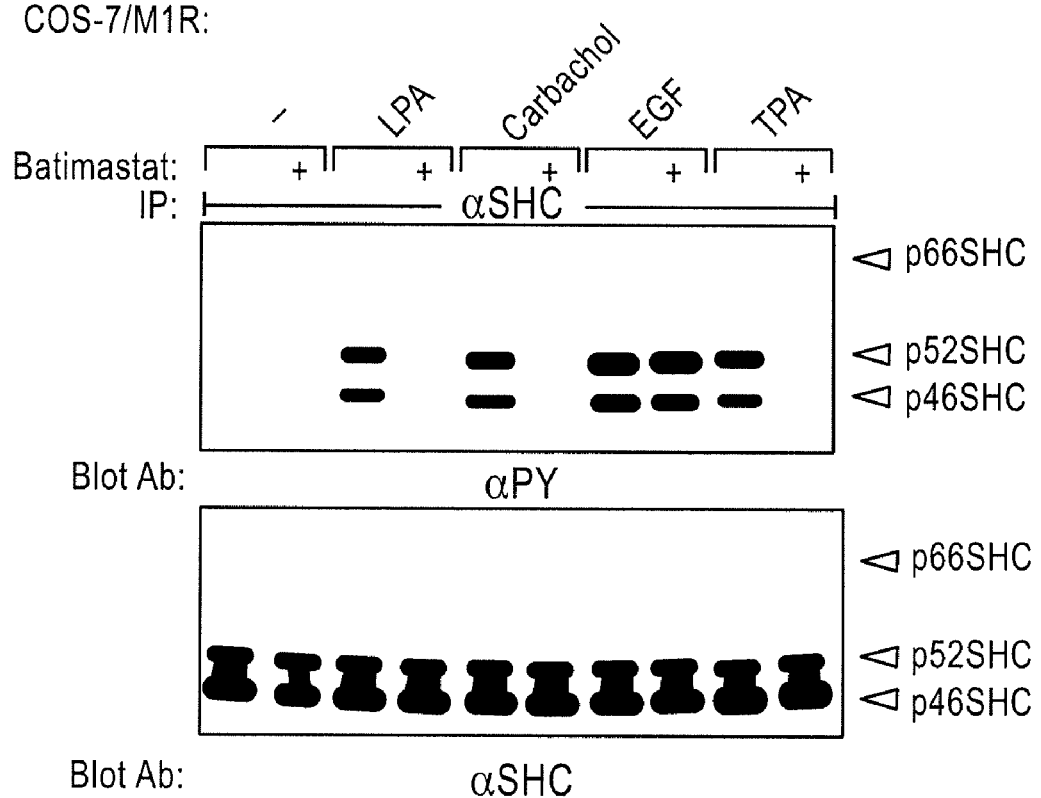

Our results demonstrate that metalloproteinase-dependent cleavage of proHB-EGF is rapidly induced upon activation of GPCRs and consequently suggest a critical and general role of this process in EGFR transactivation. We therefore investigated the effect of the metalloproteinase inhibitor batimastat in GPCR- as well as TPA-induced EGFR transactivation. In COS-7 cells, BB-94 pretreatment completely abrogated LPA- and carbachol-induced tyrosine phosphorylation of the EGFR, as well as TPA-mediated receptor activation (FIG. 4d). Since TPA- but not GPCR-mediated EGFR tyrosine phosphorylation is sensitive to PKC inhibition in COS-7 cells (data not shown), it appears that at least two distinct metalloproteinase-dependent transactivation pathways exist. Analogous results were obtained for ET-1-induced transactivation in HEK 293 cells and bradykinin-stimulated EGFR tyrosine phosphorylation in PC12 cells (data not shown). Finally, the general implication of proteolytic processing in EGFR transactivation and downstream signal transmission is demonstrated by the complete abrogation of GPCR- and TPA-induced SHC tyrosine phosphorylation by batimastat (FIG. 4e).

Figure 4F:
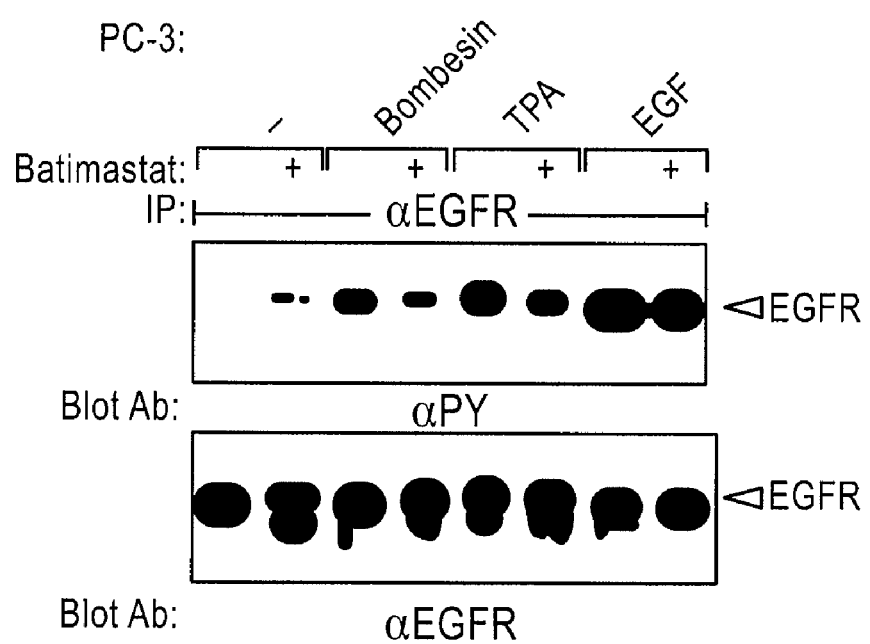
Figure 4G:
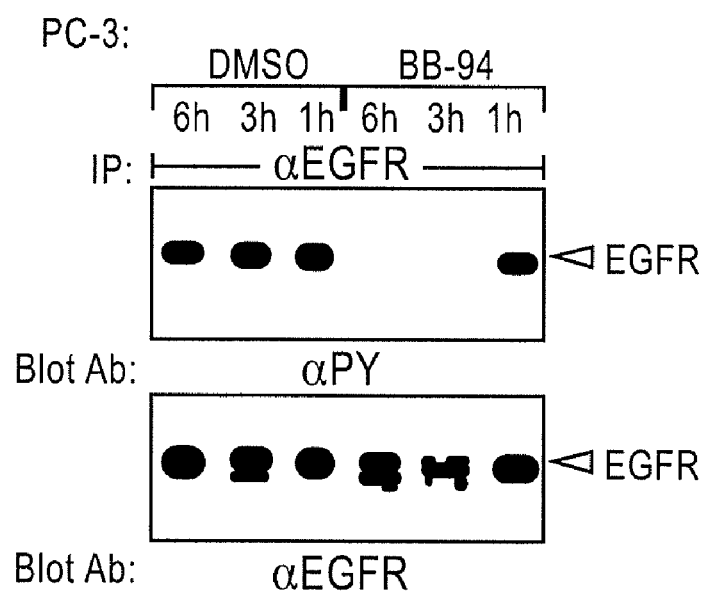

Because of the well established role of EGFR family members in the pathogenesis of a variety of cancers and the physiological abundance of GPCR ligands such as LPA, we addressed the pathophysiological significance of transactivation with the human prostate cancer cell line PC-3 which has been reported to utilize EGFR-dependent pathways for growth promotion and is also responsive to the GPCR ligand bombesin[27,28]. FIG. 4f shows that in PC-3 cells that were starved for 36 hours, bombesin, TPA and EGF induce tyrosine phosphorylation of the EGFR which is completely blocked by batimastat-treatment. Moreover, even high constitutive phosphotyrosine content of the EGFR in unstarved PC-3 cells is reduced by long-term treatment with BB-94 (FIG. 4g). All in all, our results allow the conclusion that metalloproteinase-mediated precursor cleavage represents a direct link between BombR activation, constitutive tyrosine phosphorylation of the EGFR and proliferation of human prostate cancer cells. Recently, ADAM9, a member of the metalloproteinase-disintagrin family has been reported to process proHB-EGF upon TPA treatment of Vero-H cells[24]. We were unable, however, to block EGFR transactivation with dominant-negative ADAM9 mutants in COS-7 and HEK 293 cells (data not shown) leaving the identity of the precursor processing protease unresolved.

Our findings identify the ubiquitously expressed HB-EGF precursor and a metalloproteinase activity as critical pathway elements between GPCR signals and activation of the EGFR and extend our understanding of the mechanisms that underly the multiple biological processes known to be regulated by heterotrimeric G-proteins. Based on our current state of understanding, GPCR-induced EGFR signal transactivation represents a new paradigm because it entails three different transmembrane signal transmission events: First, a ligand activates heterotrimeric G-proteins by interaction with a GPCR which results in an intracellular signal that induces the extracellular activity of a transmembrane metalloproteinase. This then results in extracellular processing of a transmembrane growth-factor precursor and release of the mature factor which, directly or via the proteoglycan matrix, interacts with the ectodomain of the EGFR leading to intracellular autophosphorylation and signal generation, Our previous findings indicate that this pathway may be utilized by a variety of GPCRs in diverse cell types and that the preferred transactivation target is the EGFR and its relatives[1-4]. The demonstration of the pathophysiological relevance of this novel mechanism in prostrate cancer cells leads us to propose that EGFR transactivation via G-protein-mediated proteolytic growth precursor processing represents a general mechanism with broad significance. Moreover, since a great variety of bioactive polypeptides as diverse as TNF-α, FAS-ligand or L-selectin are processing products of transmembrane precursors[29] that have been connected to pathophysiological disorders, our findings shed new light on the importance of membrane-associated proteinases as targets for disease intervention strategies.

LIST OF REFERENCES

1. Daub et al., EMBO J. 16, 7032-7044 (1997)
2. Daub et al., Nature 379, 557-560 (1996)
3. Luttrell et al., Curr. Opin. Cell Biol. 11, 177-183 (1999)
4. Hackel et al., Curr. Opin. Cell Biol. 11, 184-189 (1999)
5. Eguchi et al., J. Biol. Chem. 273, 8890-8896 (1998)
6. Luttrell et al., J. Biol. Chem. 272, 4637-4644 (1997)
7. Keely et al., J. Biol. Chem. 273, 27111-27117 (1998)
8. Tsai et al., EMBO J. 16, 4597-4605 (1997)
9. Li et al., EMBO J. 9, 2574-2583 (1998)
10. Seedorf et al., J. Biol. Chem. 266, 12424-12431 (1991)
11. Kovalenko et al., Cancer Res. 54, 6106-6114 (1994)
12. Vogel et al, Science 259, 1611-1614 (1993)
13. Matco et al., Immunotechnology 3, 71-81 (1997)
15 14. Massaigué & Pandiella, Annu. Rev. Biochem. 62, 515-541 (1993)
15. Green et al, BioEssays 18, 639-646 (1996)
16. Bosenberg et al., J. Cell Biol. 122, 95-101 (1993)
17. Goishi et al., Mol. Biol. Cell 6, 967-980 (1995)
18. Dethlefsen et al., C.J. Cell. Biochem. 69, 143-153 (1998)
19. Zwick et al., J. Biol. Chem. 272, 24767-24770 (1997)
20. Raab & Klagsbrun, Biochim. Biophys. Acta 1333, F179-F199 (1997)
21. Naglich et al., Cell 69, 1051-1061 (1992)
22. Mitamura et al., J. Biol. Chem. 270, 1015-1019 (1995)
23. Chen et al., EMBO J. 15, 1037-1044 (1996)
24. Izumi et al., EMBO J. 17, 7260-7272 (1998)
25. Wojtowicz-Praga et al., Investigational New Drugs 15, 61-75 (1997)
26. Brown et al., J. Biol. Chem. 273, 17258-17268 (1998)
27. Ching et al., Mol. Cell Biochem. 126, 161-158 (1993)
28. Hoosein et al., J. Urol. 149, 1209-1213 (1993)
29. Werb, Cell 91, 439-442 (1997)
30. Schäggar & von Jagow, Anal. Biochem. 166, 368-379 (1987)
31. Amour et al., FEBS Lett. 435, 39-44 (1998)

The invention claimed is:

1. A method for modulating a G protein mediated signal transduction in in vitro comprising:
   providing a cell having epidermal growth factor receptor (EGFR) comprising an extracellular domain wherein the cell has a G protein mediated signal transduction pathway and one or more tyrosine residues on said EGFR are phosphorylated based on the activation of the G protein mediated signal transduction pathway, the extracellular domain of said EGFR is capable of binding to an EGFR ligand, and said ligand is generated from the precursor of said ligand by cleavage of said precursor with a metalloproteinase from ADAM family of metalloproteinases;
   contacting said cell with a compound capable of activating said G protein mediated signal transduction pathway in the absence and presence of an inhibitor of said metalloproteinase wherein said inhibitor blocks the release of said ligand from said precursor;
   measuring tyrosine phosphorylation of said EGFR in said cell to determine whether said G protein mediated signal transduction pathway has been activated;
   comparing the levels of tyrosine phosphorylation of said EGFR in said cell in the absence and presence of said inhibitor wherein a reduction in the level of tyrosine phosphorylation of said EGFR in the presence of said inhibitor indicates that releasing said EGFR ligand from said precursor is critical for activation of said G protein mediated signal transduction pathway in said cell and said activation is dependent on the interaction between the extracellular domain of said EGFR and said EGFR ligand.

* * * * *